United States Patent
Damadian et al.

(10) Patent No.: US 8,934,990 B1
(45) Date of Patent: Jan. 13, 2015

(54) LOCALIZED RF HEATING

(75) Inventors: Raymond V. Damadian, Woodbury, NY (US); Lawrence A. Minkoff, Lattingtown, NY (US); Jan Votruba, Bernardston, MA (US)

(73) Assignee: Fonar Corporation, Melville, NY (US)

( * ) Notice: Subject to any disclaimer, the term of this patent is extended or adjusted under 35 U.S.C. 154(b) by 0 days.

(21) Appl. No.: 13/073,271

(22) Filed: Mar. 28, 2011

Related U.S. Application Data

(63) Continuation of application No. 13/039,866, filed on Mar. 3, 2011, now abandoned.

(60) Provisional application No. 61/339,453, filed on Mar. 4, 2010.

(51) Int. Cl.
*A61F 7/00* (2006.01)
*A61N 5/00* (2006.01)

(52) U.S. Cl.
USPC .......................................................... 607/101

(58) Field of Classification Search
USPC .......................................................... 607/101
See application file for complete search history.

(56) References Cited

U.S. PATENT DOCUMENTS

| | | | | |
|---|---|---|---|---|
| 4,230,129 A * | 10/1980 | LeVeen | ........................ | 607/154 |
| 4,462,412 A * | 7/1984 | Turner | .......................... | 607/98 |
| 5,097,844 A * | 3/1992 | Turner | ........................ | 607/156 |
| 5,284,144 A * | 2/1994 | Delannoy et al. | ............. | 600/412 |
| 5,492,122 A * | 2/1996 | Button et al. | ................. | 600/411 |
| 6,023,166 A | 2/2000 | Eydelman | | |
| 6,028,429 A | 2/2000 | Green et al. | | |
| 6,107,974 A | 8/2000 | Votruba et al. | | |
| 6,249,121 B1 * | 6/2001 | Boskamp et al. | ............. | 324/318 |
| 6,677,753 B1 | 1/2004 | Danby et al. | | |
| 6,807,446 B2 * | 10/2004 | Fenn et al. | ..................... | 607/101 |
| 7,123,010 B2 * | 10/2006 | Krockel | ........................ | 324/318 |
| 7,466,130 B1 | 12/2008 | Votruba et al. | | |
| 7,573,432 B1 | 8/2009 | Eydelman et al. | | |
| 7,701,209 B1 | 4/2010 | Green | | |
| 7,769,468 B2 * | 8/2010 | Turner et al. | .................. | 607/100 |
| 8,055,326 B1 * | 11/2011 | Dworkin et al. | ............. | 600/422 |
| 8,129,991 B2 | 3/2012 | Wahl et al. | | |
| 2007/0118193 A1 * | 5/2007 | Turner et al. | .................. | 607/101 |
| 2009/0132015 A1 * | 5/2009 | Miller et al. | ................... | 607/101 |
| 2010/0318162 A1 * | 12/2010 | Rose | ............................. | 607/101 |

* cited by examiner

*Primary Examiner* — Ronald Hupczey, Jr.
(74) *Attorney, Agent, or Firm* — Lerner, David, Littenberg, Krumholz & Mentlik, LLP

(57) ABSTRACT

An apparatus is provided for generating focused radio frequency. The apparatus may include multiple coils, and the multiple coils can be actuated so as to generate focused energy at a focal location within the body of a subject such as a human or non-human animal while minimizing heating at the skin of the subject. A first central coil and a second central coil that are placed adjacent to each other. The apparatus also comprises a first focusing coil and a second focusing coil. The first central coil and the second central coil are placed between the first focusing coil and the second focusing coil. The first focusing coil and the second focusing coil generate a radio frequency field that is 180 degrees out of phase from a radio frequency field generated by the first central coil and the second central coil.

13 Claims, 15 Drawing Sheets

LOCALIZED RF HEATING

CROSS-REFERENCE TO RELATED APPLICATIONS

This application is a continuation of U.S. application Ser. No. 13/039,866, filed on Mar. 3, 2011, now abandoned which claims the benefit of the filing date of U.S. Provisional Patent Application No. 61/339,453, filed Mar. 4, 2010, the disclosure of which is hereby incorporated herein by reference.

BACKGROUND OF THE INVENTION

1. Field of the Invention

The present inventions relate to the treatment of a subject such as a human or non-human animal by application of focused radio frequency ("RF") energy. More specifically, the present invention relates to localized RF heating as, for example, heating of a region within the body, such as a tumor. The application of RF energy desirably occurs in the "near field" of the RF coils.

2. Description of Related Art

Previous use of RF to treat tumors made use of a needle probe that would be inserted into the tumor. The needle was then attached to an RF source, operating at about 500 kHz. The mechanism was to heat the tumor to about 50-60 C causing its death. The heating was accomplished more from resistive heating rather than to absorption of the RF such as in a microwave oven.

Medically there are other uses for RF such as Diathermy the radio frequency energy is used to heat muscles, joints, decrease inflammation, and increase blood flow. However, in none of these applications is the RF focused, Coils are used in a general location without regard to a particular target.

SUMMARY OF THE INVENTION

One aspect of the present invention provides apparatus which incorporates a plurality of RF coils mounted adjacent one another and a driver circuit for driving the coils so as to apply a strong RF field at a focus location within the body of a subject while minimizing heating of the skin of the subject. For example, the driver circuit may be arranged to actuate the coils in alternating sequence.

A further aspect of the invention includes methods of heating tissues in the body of a subject using a plurality of coils mounted adjacent one another. Desirably, the method includes actuating the coils at radio frequencies so that the coils apply a strong RF field at a focus location within the body while minimizing heating of the subject's skin.

In one embodiment of the invention, an apparatus for generating focused radio frequency comprises a first central coil and a second central coil adjacent to each other; a first focusing coil; and a second focusing coil; wherein the first central coil and the second central coil are placed between the first focusing coil and the second focusing coil, wherein the first focusing coil and the second focusing coil generate a radio frequency field that is 180 degrees out of phase from a radio frequency field generated by the first central coil and the second central coil.

In another embodiment of the invention, an apparatus of generating focused radio frequency comprises a cylindrical housing of conductive material; a main coil disposed in the cylindrical housing; and a cylindrical-shaped focusing coil placed at one end of the cylindrical housing; wherein the cylindrical-shaped focusing coil generate a radio frequency field that is 180 degrees out of phase from a radio frequency field generated by the main coil.

In a further embodiment of the invention, an apparatus of generating focused radio frequency comprises a cylindrical housing of non-conductive material; a plurality of radio frequency coils disposed on an outer surface of the cylindrical housing with space between each other, wherein each radio frequency coil operates at a resonant frequency different from other radio frequency coils; a cylindrical surface of conductive material surrounding the plurality of radio frequency coils, wherein a plurality of holes are disposed through the cylindrical surface; a plurality of radio frequency input circuits, each respective radio frequency input circuit connects to a respective radio frequency coil through a respective hole; and a power switch circuit connected to the plurality of radio frequency input circuits and configured to control the radio frequency coils based on a predetermined time sequence.

DETAILED DESCRIPTION

In this invention the RF desirably is applied externally to the body from several sources. Each source will be of sufficiency low power as to not cause any ill effects to the individual under treatment. At the point that these multiple sources are aimed (the focus location) the energy will be at a level that will heat the tissue. For example, if a tumor is present, the RF energy desirably heats the tumor causing its death.

Because of possible interference of multiple RF coils being turned on at once, one alternative embodiment would be to pulse the different sources sequentially so that no two are on simultaneously. In a modification of this embodiment each RF coil could be tuned to a slightly different frequency, thus avoiding interference. Alternatively, the RF coil could be moved in such a manner that the focused point is always hit and the surrounding tissue moves in and out of the RF field.

This internal heating of the tumor can be followed in an MRI system. Magnetic Resonance is well suited to follow the temperature rise deep in the body and determine when the target temperatures are reached. In one embodiment of the invention, the apparatus for heating the tumor would be placed in the MRI system.

The choice of frequencies that would be used would depend on several issues such as the RF absorption of the targeted tissue, the mechanism of the cells destruction, and absorption of tissue surrounding the focus location, and scattering of the RF by bone and other organ interfaces.

The choice of the frequencies could also determine the structure and type of RF coil used in the invention. In general all the RF coils can consist of several nested coils. With the inner coils 120 and 130 generating the main field and outer coils 110 and 140 limiting and focusing the RF beam. (See FIGS. 1 and 2). The Focusing Coils 110 and 140 generate an RF field that is 180 degrees out of phase from the central main field. The beam would be designed to be as narrow as possible. The length of the beam would only have to be about 6 inches or half the reach across the human body.

Multiple sources of focused RF could then be aimed at a single point within the body, or a single coil could be moved to avoid surface heating but still aimed at a single point within the body. Either approach would still be capable of heating the tumor deep within the body and while keeping the surface heating to a minimum.

Figure 3:
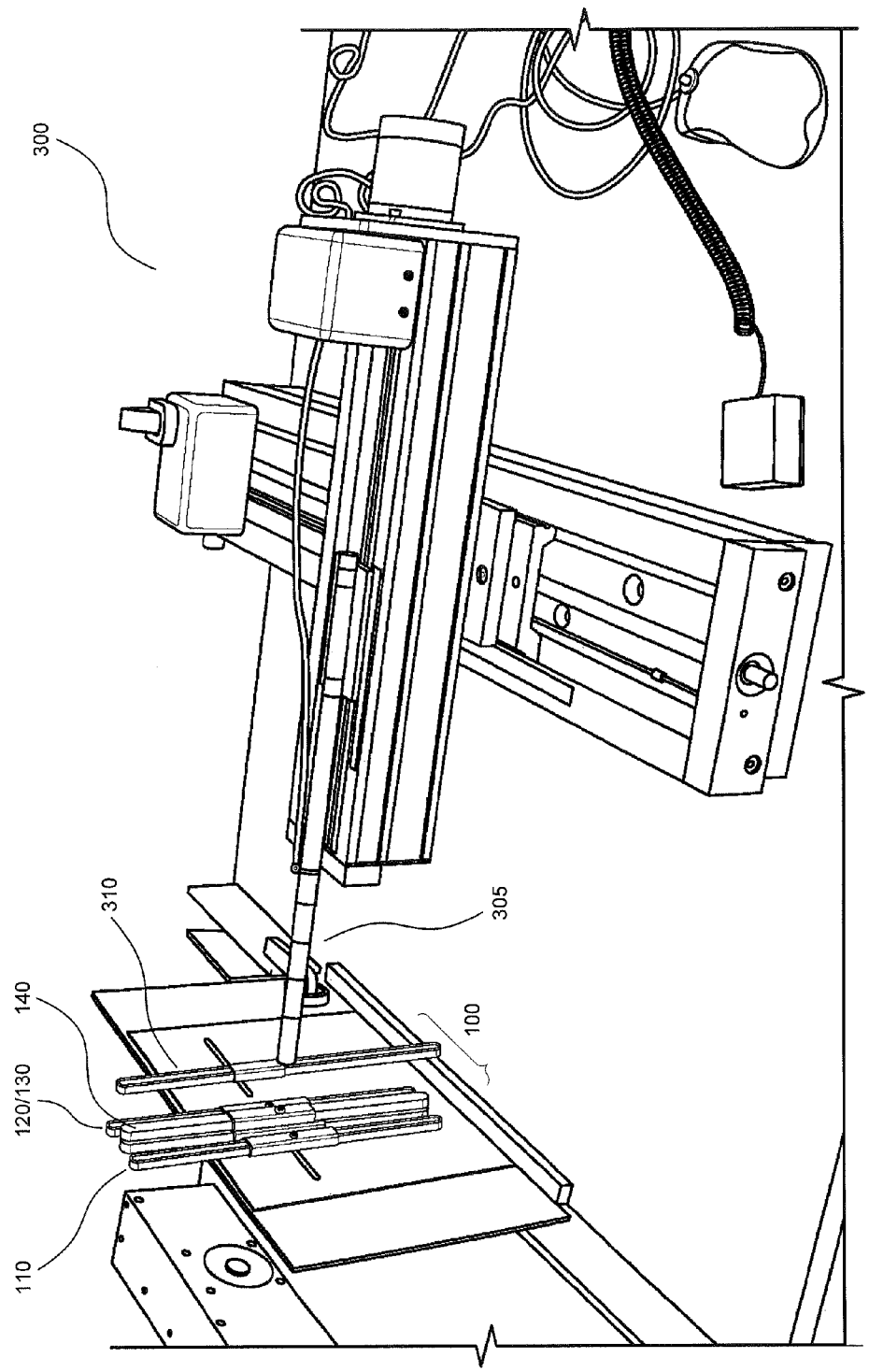
FIG. 3 shows an example experimental setup in accordance with aspects of the invention.
Figure 4:
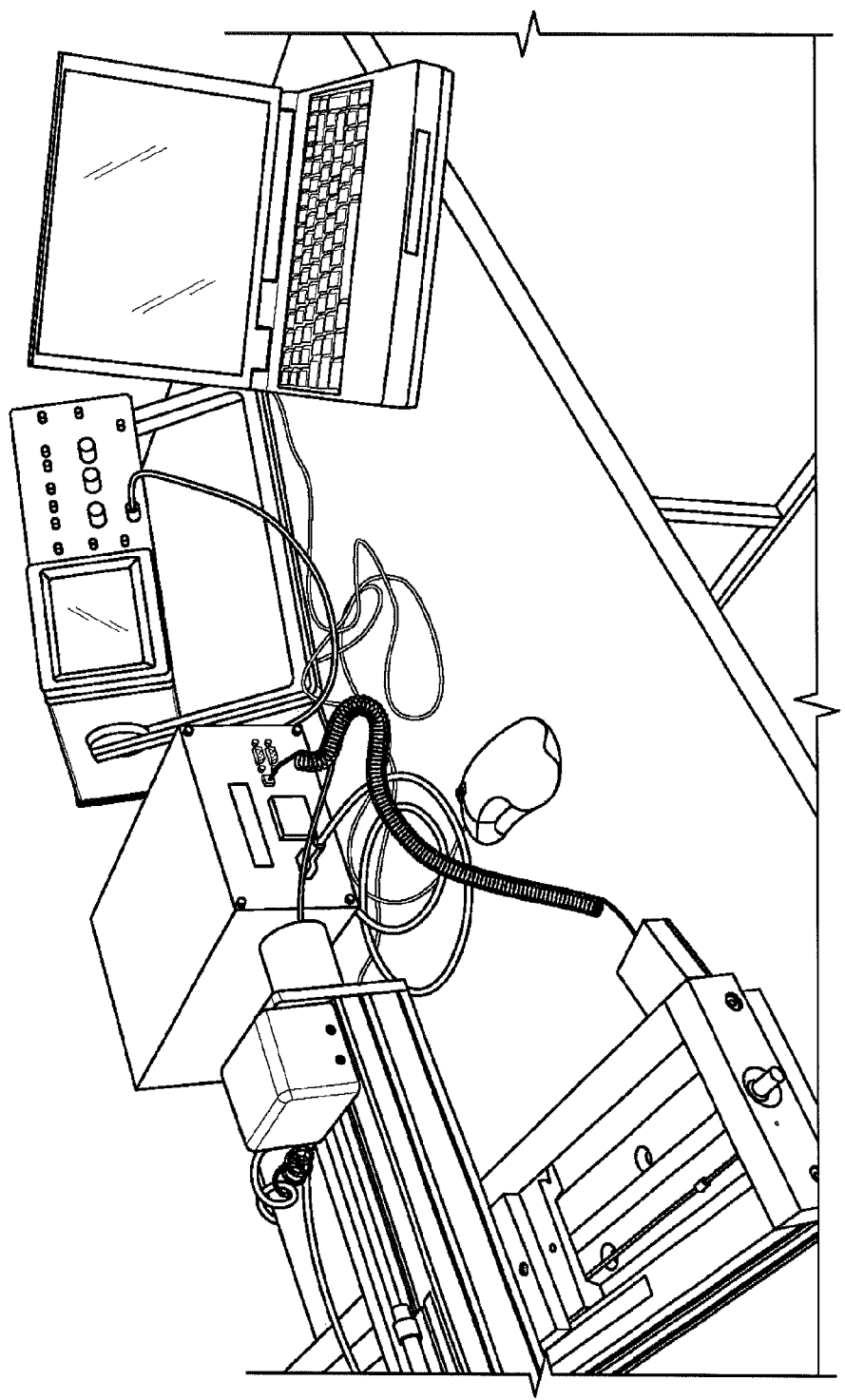
FIG. 4 shows another example experimental setup in accordance with aspects of the invention.
Figure 5:
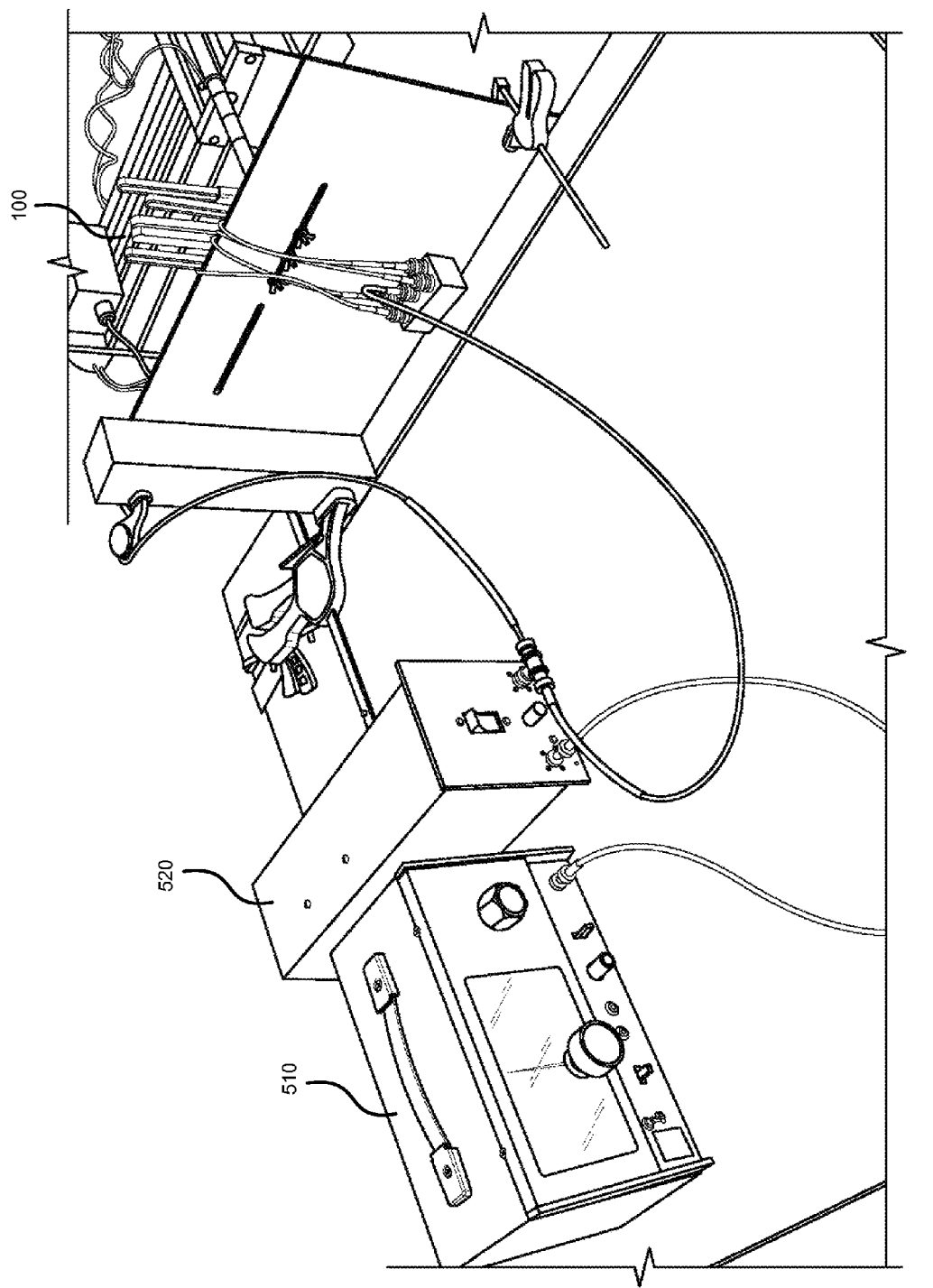
FIG. 5 shows a further example experimental setup in accordance with aspects of the invention.
Figure 6:
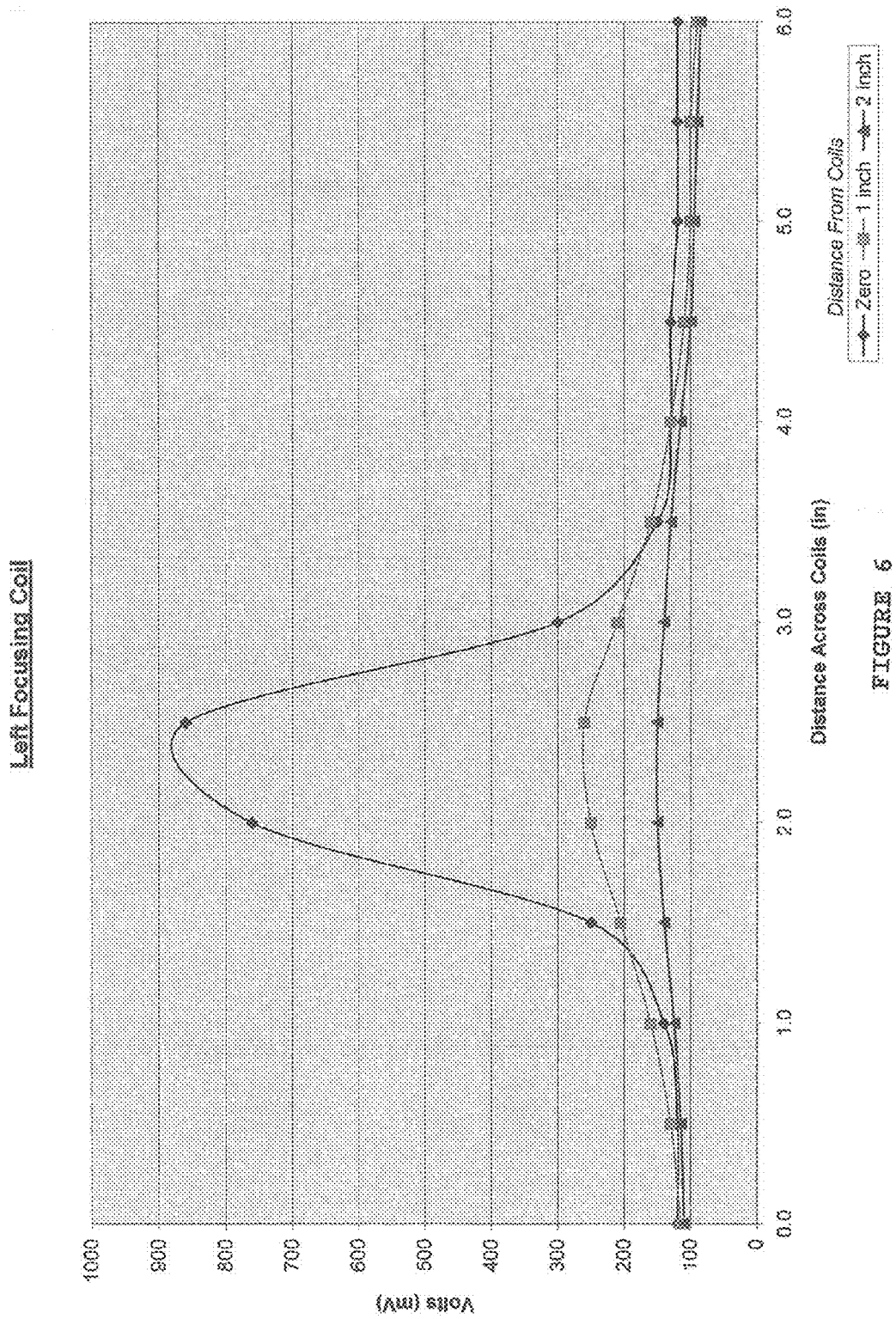
FIG. 6 shows an example RF energy plot generated in accordance with aspects of the invention.

In the first approach to focusing RF (FIG. 1) two central coils 120 and 130 are used. They are flanked by two focusing coils 110 and 140 on either side. FIGS. 3, 4 and 5 collectively show the experimental setup 300 used to map the RF fields. A signal generator 510 (FIG. 5) is electrically connected to the RF coil array 100 through an amplifier 520. At the end of the wooden dowel 305 (FIG. 3) is the sensor coil 310 that can be passed across the array 100 of RF coils 110-140 at different distances. The first graph labeled "Left Focusing Coil" (FIG. 6) shows the amount of RF energy detected on the oscilloscope (FIG. 4) when only the left focusing coil 110 is energized. The three plots show the sensor being passed at different distance from the coil array 100.

Figure 7:
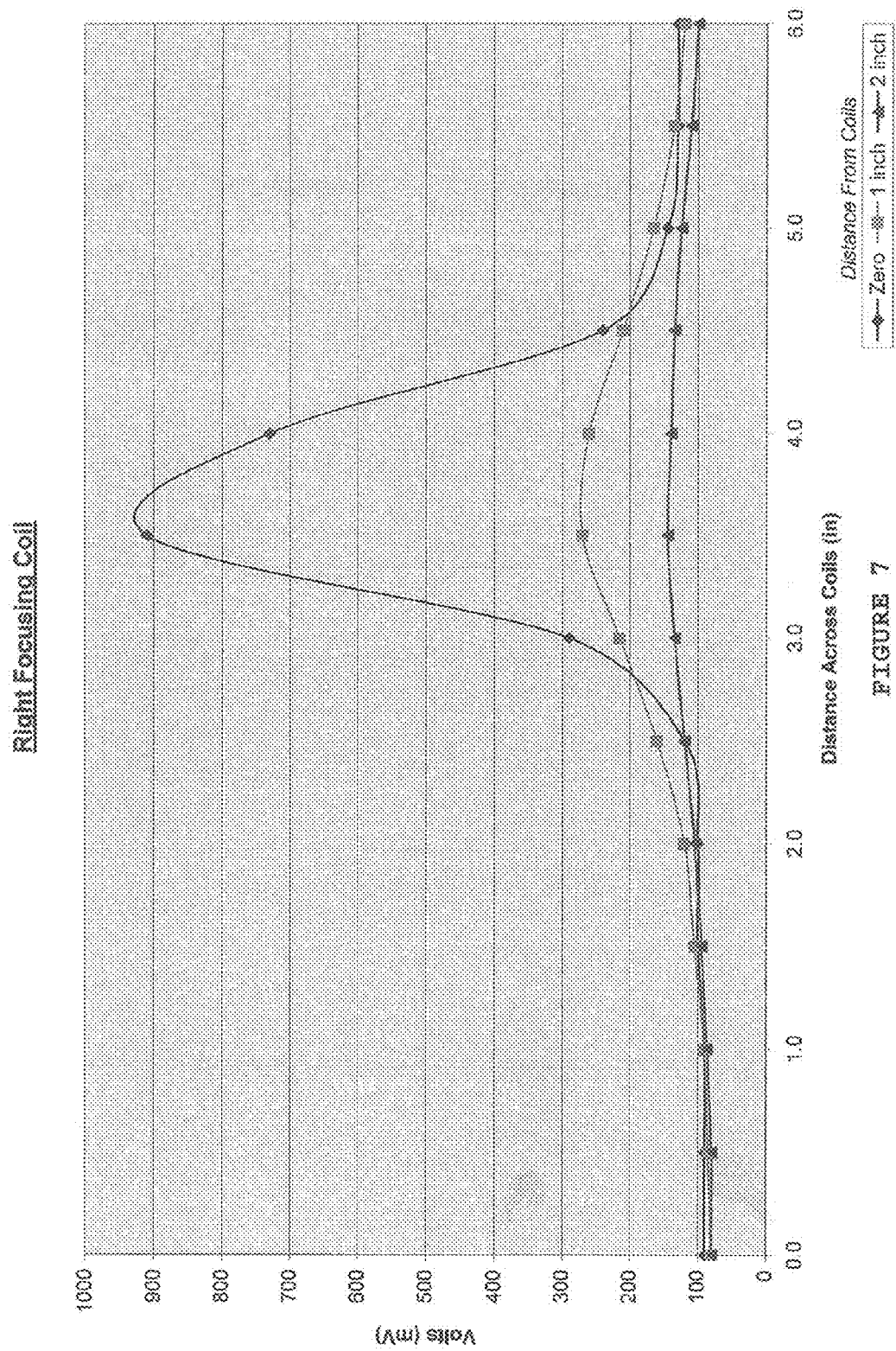
FIG. 7 shows another example RF energy plot generated in accordance with aspects of the invention.
Figure 8:
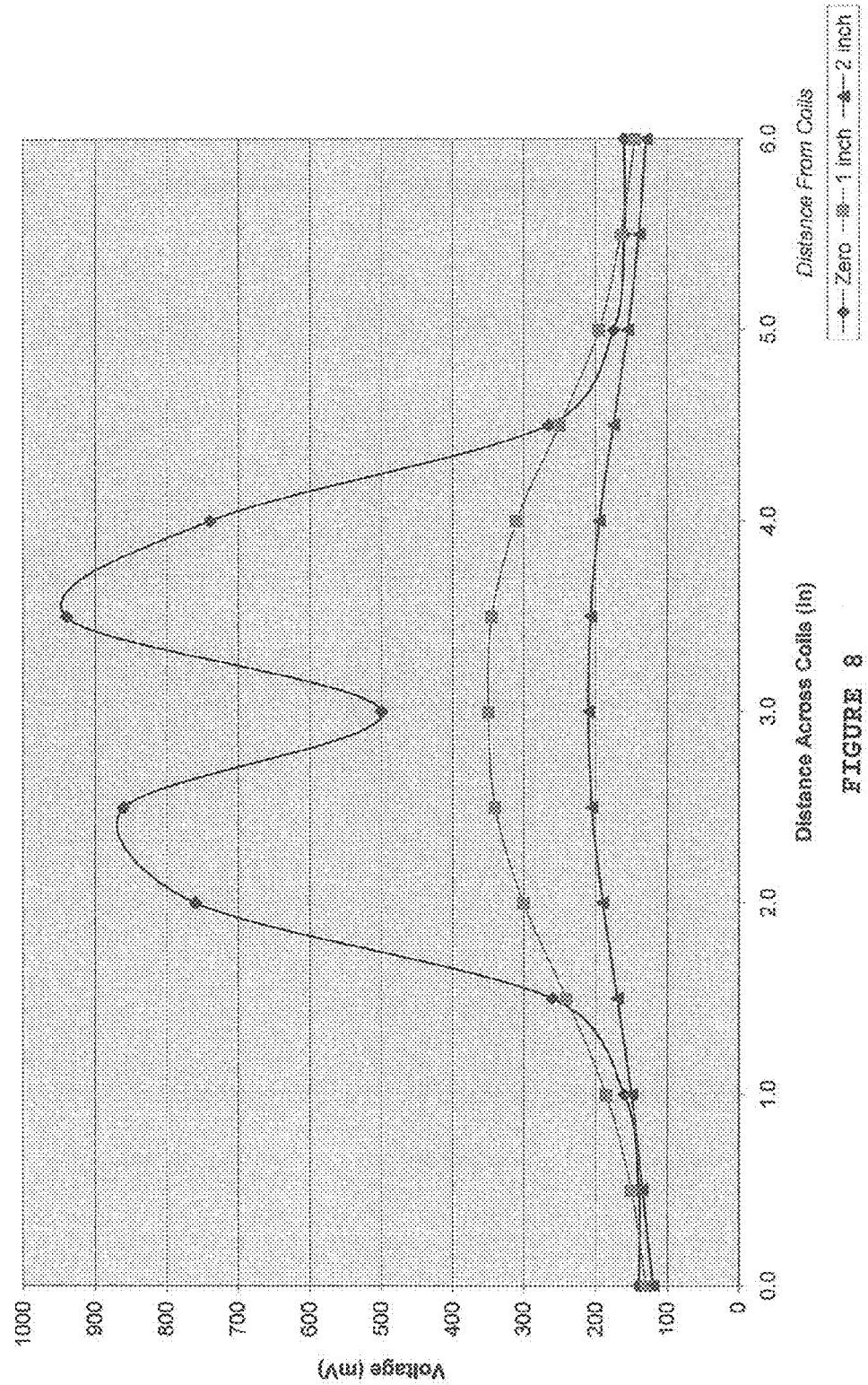
FIG. 8 shows a further example RF energy plot generated in accordance with aspects of the invention.

The next graph labeled "Right Focusing Coil" (FIG. 7) is similar to the previous plots only the right coil 140 is energized. Similarly with the graph labeled "Both Focusing Coils" (FIG. 8) the plots show energy distributions from both Focusing Coils 110 and 140.

Figure 1:
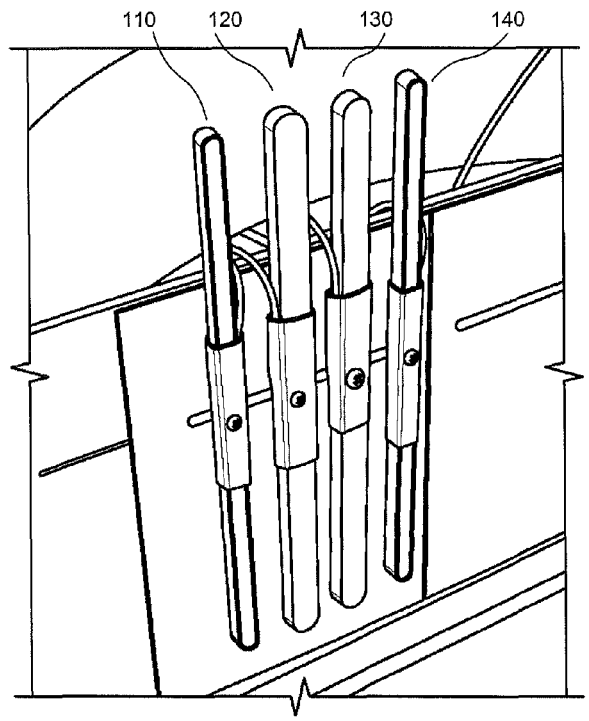
FIG. 1 shows an example apparatus in accordance with aspects of the invention.
Figure 9:
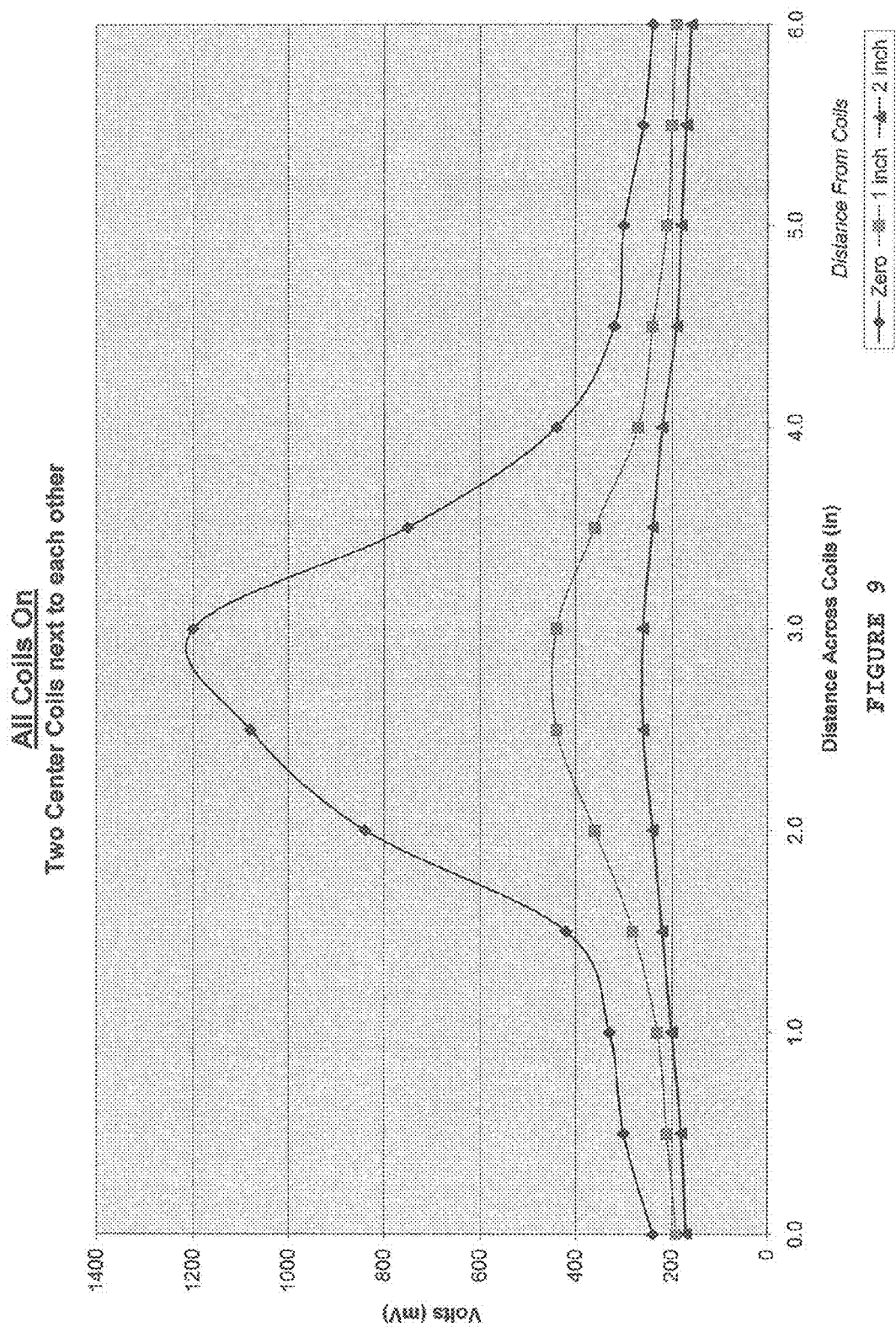
FIG. 9 shows yet another example RF energy plot generated in accordance with aspects of the invention.
Figure 10:
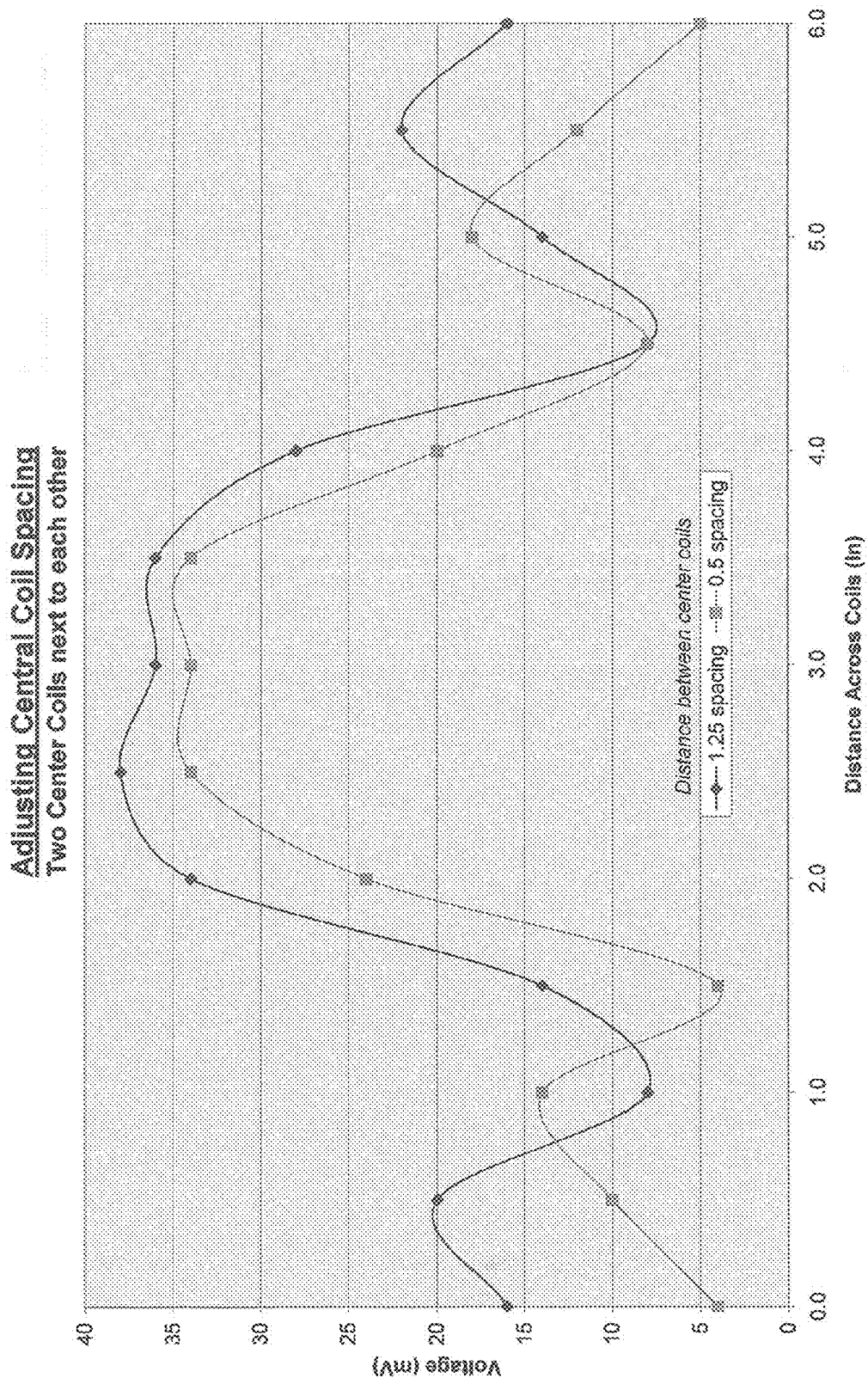
FIG. 10 shows another example RF energy plot generated in accordance with aspects of the invention.

The graph labeled "All Coils On" (FIG. 9) shows the RF field produced in an array as in FIG. 1 with two central coils 120 and 130 next to each other. The effect of adjusting the distance between the two central coils 120 and 130 is illustrated in the graph labeled "Adjusting Central Coil Spacing" (FIG. 10).

Figure 2:
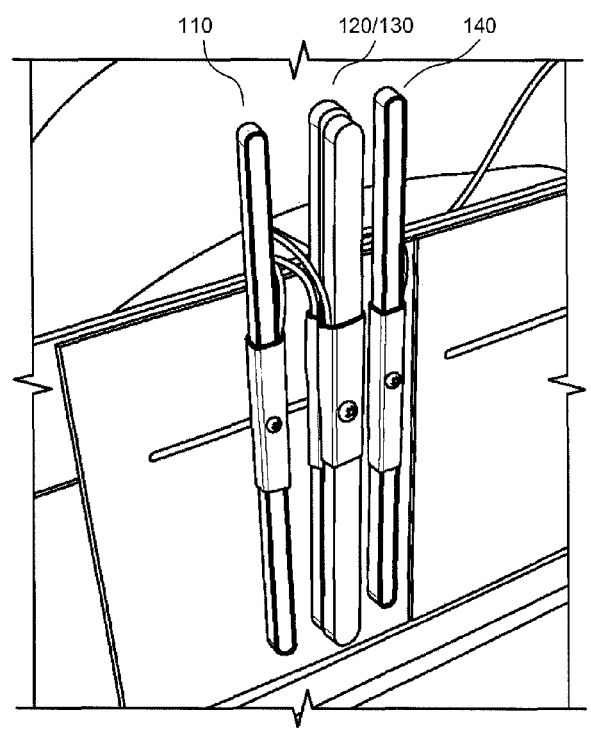
FIG. 2 shows another example apparatus in accordance with aspects of the invention.
Figure 11:
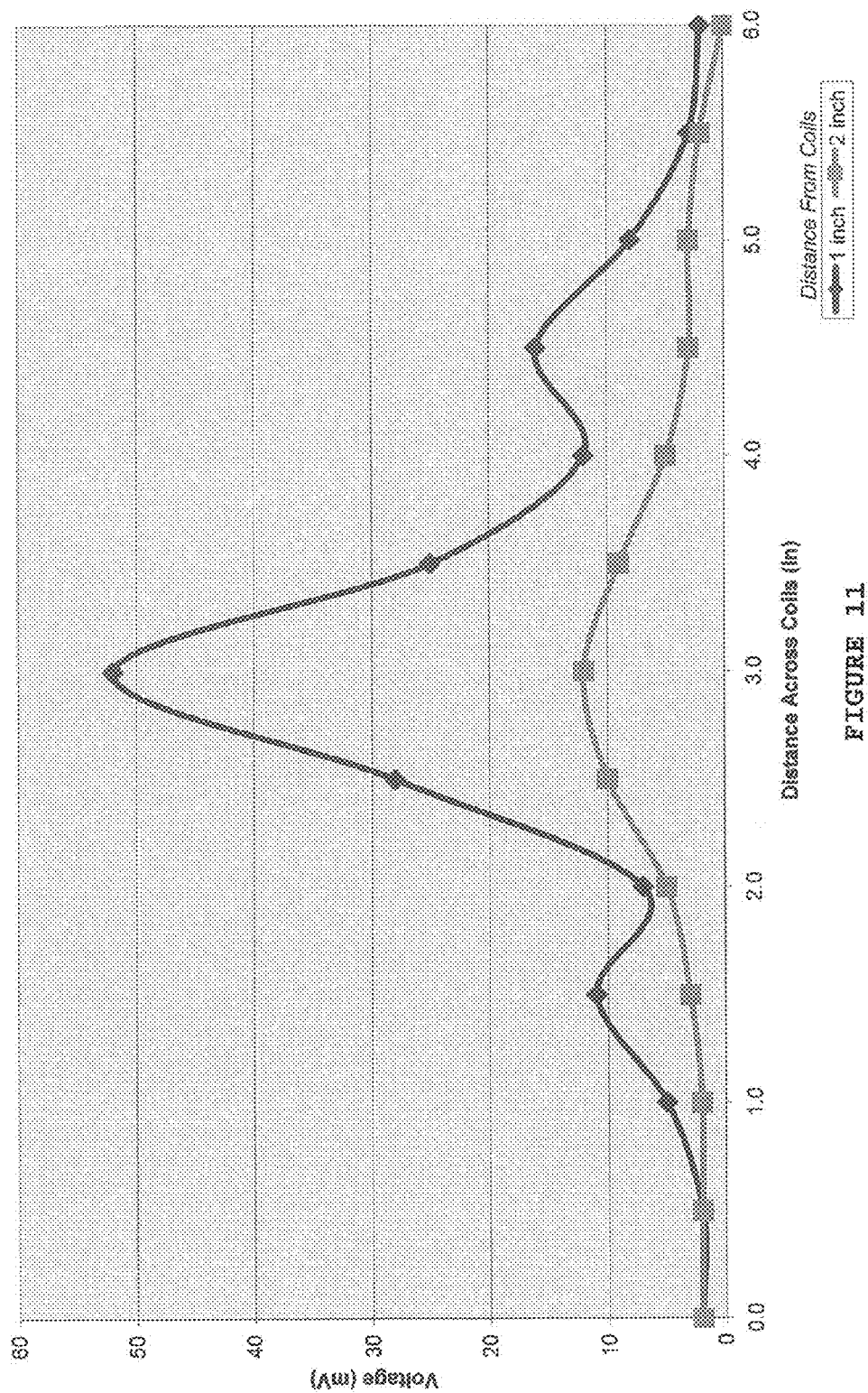
FIG. 11 a further example RF energy plot generated in accordance with aspects of the invention.

To try to increase the amount of RF Focusing, the Central Coils 120 and 130 were placed on top of each other (FIG. 2). This increased the RF field generated by the central main coil 120/130 and put double the number of ampere tunes in the main coil 120/130 as the side Focusing Coils 110 and 140. The result is a sharper focused RF beam as seen in the graph labeled "Single Center Coil" (FIG. 11).

Figure 12:
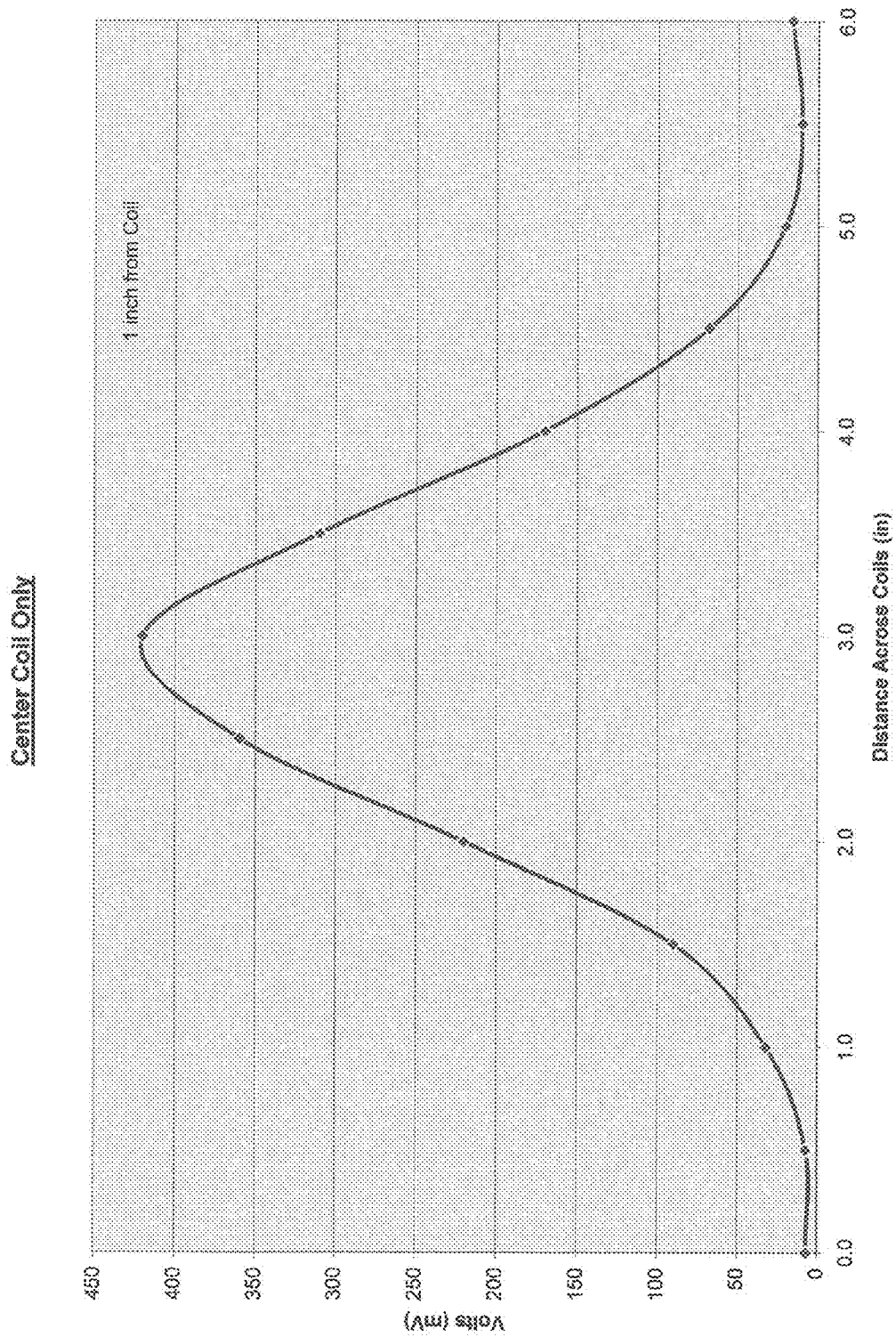
FIG. 12 shows yet another example RF energy plot generated in accordance with aspects of the invention.

As a point of reference the graph labeled "Center Coil Only" (FIG. 12) has only the main coil 120/130 on with none of the focusing coils 110 and 140. The plot is done at the same 1 inch distance from the coils as was the previous graphs, "Single Center Coil" (FIG. 11). Without the focus coils 110 and 140, the coil profile is as expected, covering a range from 1 inch to 5 inches on the x-axis. When the focusing coils 110 and 140 are on, the range of the profile is from 2 inches to 4 inches. The difference in voltage measured is a function of power distribution, power going to one coil as compared to four coils.

Figure 13:
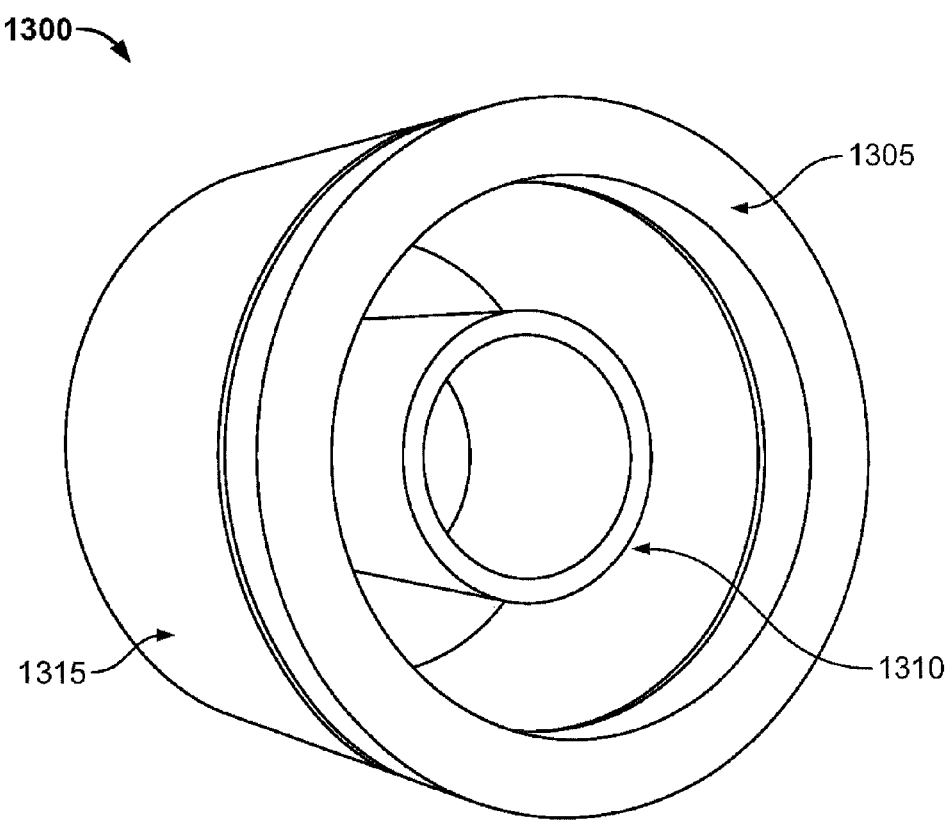
FIG. 13 shows an example apparatus in accordance with aspects of the invention.

A refinement 1300 of the previously described RF coil array is shown in the illustration of FIG. 13. The central (Main Coil) coil 1310 is housed in an Aluminum (Copper or any other highly conducive metal would do) housing 1315. This limits the RF fringe field and helps direct the field in the desired direction. The geometry of the housing 1315 could be simply a metal can or more sophisticated as parabolic or elliptical.

A Focusing Coil 1305 is placed at the mouth of the metal housing 1315 and carried current 180 degrees out of phase with the main coil. The amount of current in the Focusing Coil 1305 relative to the Main Coil 1310 will determine the nature and shape of the RF Beam. In one embodiment two of these nested coils are placed on the same axis on either side of the patient. This permits them to work together to produce a better controlled RF Beam.

It is known that a malignant tissue can be destroyed by temperatures which a healthy tissue is still able to tolerate without being damaged.

The concentration of thermal energy can be accomplished by a special arrangement of an array 1400 of RF coils surrounding the body and driven by a special power switching time sequence.

Many attempts have been made to destroy tumors by electromagnetic field at microwave frequencies in the past. The problem with this approach is that the near-field regime does not hold well resulting in contamination of the sample by the electric component of the field. As a result, the localization of thermal energy was unpredictable and the heating was happening in wrong places in the body. In modern times, these problems have been solved by using low-frequency RF. In this case, it is feasible to work in pure quasi-stationary mode with RF magnetic fields. There are, however, still difficulties related to a strong field close to the RF applicators resulting in overheating of the healthy tissue in the surface areas of the body. A progress has been made in U.S. Pat. No. 4,230,129 operating at 13.56 MHz. In this patent, the undesirable superficial increase in ambient temperature, which would ultimately prevent the device from delivering the desired temperature to the tumor inside the body is addressed. Two RF coils are mechanically moved, circumferentially around the body while maintaining the targeted area in focus.

In one embodiment of the present invention presented herein, the mechanical motion of two opposite RF coils is replaced by a stationary multiplicity (array) of RF coils and by a special time on-and-off power switching sequence among the said coils so as not to affect the surrounding tissue adversely.

Figure 14:
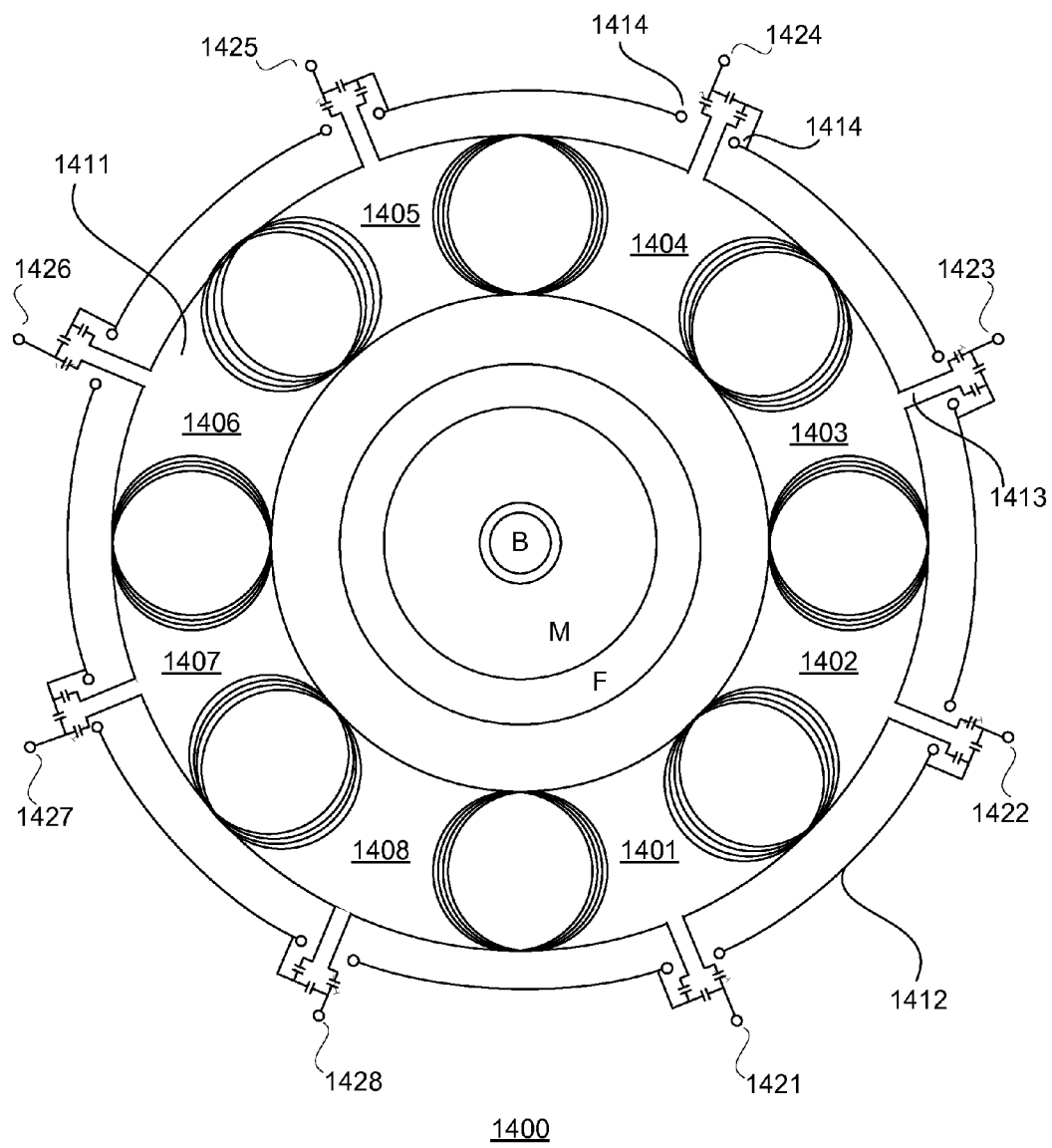
FIG. 14 shows another example apparatus in accordance with aspects of the invention.
Figure 15:
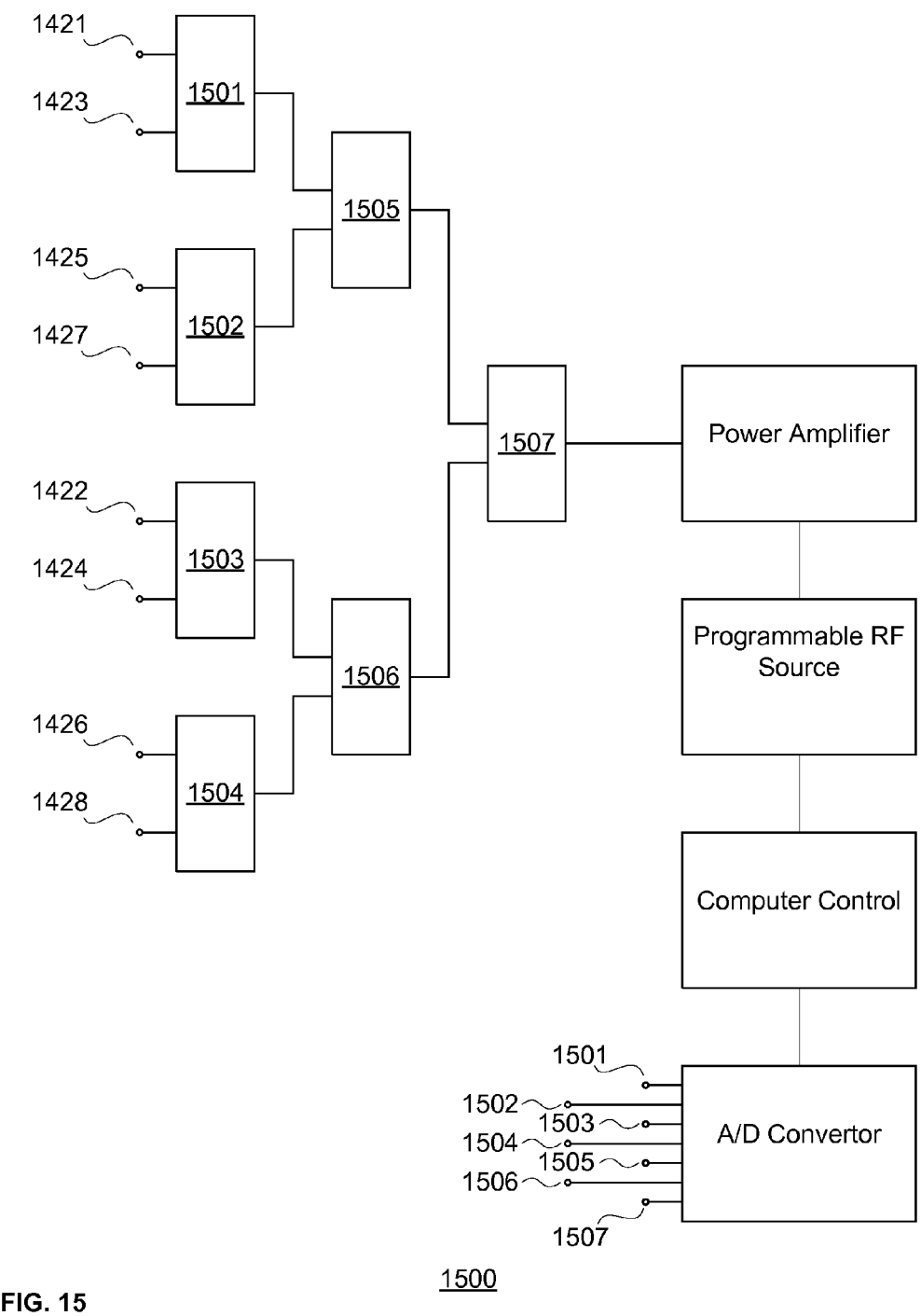
FIG. 15 shows an example RF power switching circuit and an example timing sequence in accordance with aspects of the invention.
Figure 16:
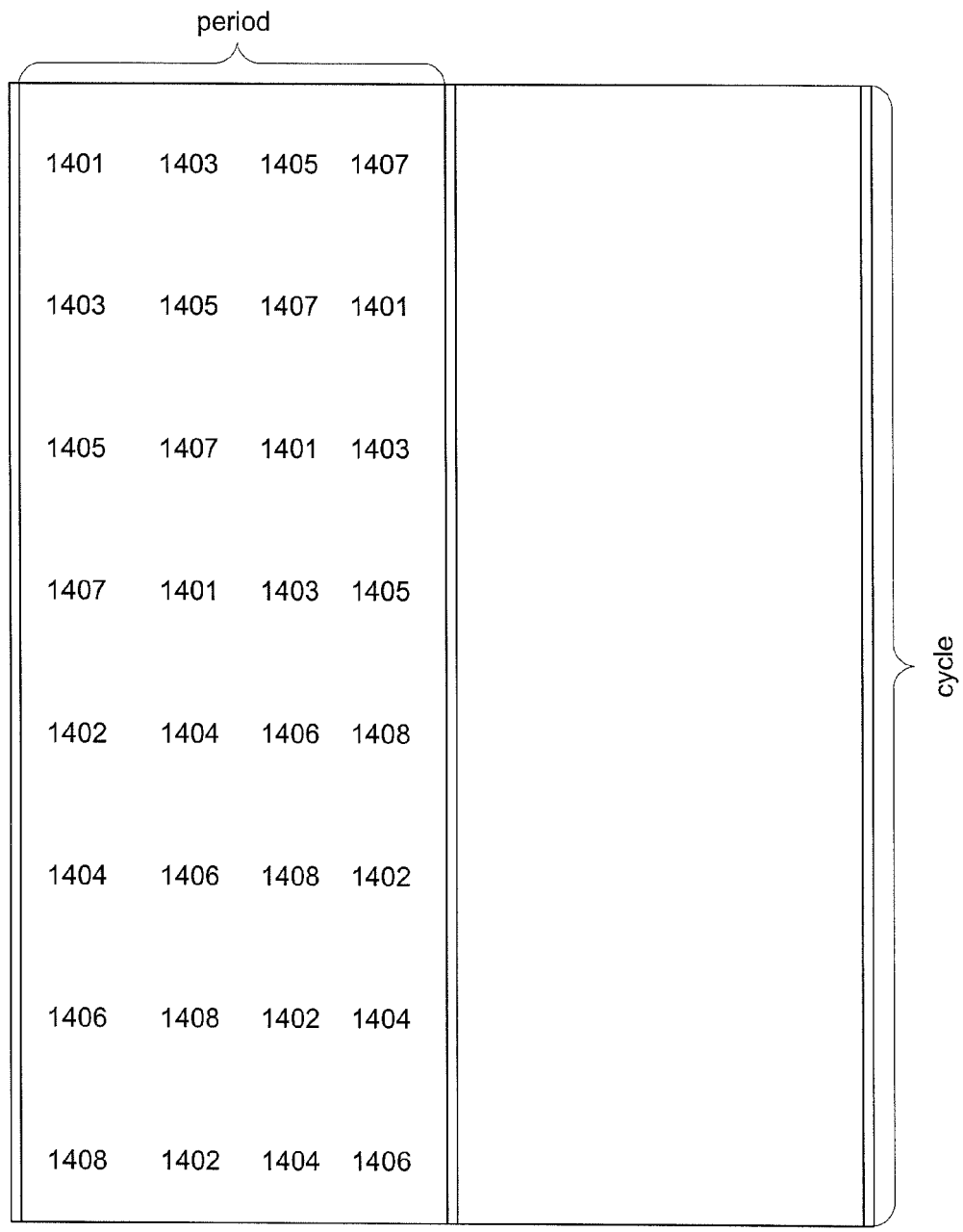
FIG. 16 shows a table providing an example RF pulse sequence in accordance with aspects of the invention.

In one embodiment, shown schematically in FIG. 14 a plastic cylindrical surface 1411, preferably 20" in diameter and 10" high, carries light circular overlapped RF coils. (For visualization, coils 1401-1408 are not correctly perspective in the diagram). The assembly of eight RF coils 1401-1408 is surrounded concentrically by a RF mirror. The mirror is a cylindrical surface 1412, preferably 30" in diameter and 16" high, made from solid copper sheet or from a thin copper foil attached to a plastic cylindrical carrier. In this conductive cylinder there are eight holes 1413 for the RF input circuits 1421-1428 to the RF coils 1401-1408. These holes 1413 have rounding inserts 1414 to prevent arcing discharges at high power levels. The RF coils 1401-1408 are matched to 50Ω when the whole assembly is loaded by a typical body or by a phantom with equivalent loading characteristics. While the RF coils are geometrically decoupled to diminish a cross talk among them, it is desirable to operate them at different resonant frequencies to further increase their electrical independence. The preferred set of frequencies are: 13.6, 13.8, 14.0, 14.2, 14.4, 14.6, 14.8 and 15.0 in MHz. The input circuits 1421-1428, with matching and tuning circuits are connected to an aggregate 1500 of seven RF power switches 1501-1507 shown in FIG. 15. The purpose of the switches 1501-1507 is to enable time sequencing of RF power in the RF coils. A chosen time sequence then provides a relaxation time for the surface areas of the body to cool down before the next heat RF pulse arrives. The duration of RF pulses could be one second, for example. As an embodiment sequence shown in a form of a table 1600 in FIG. 16 has a ratio power ON/power OFF=1:7 and 1:11 and the ratio or the adjacent coils to be energized is 1:4 as can be checked by an inspection of table 1600.

For the best mode for carrying out or practicing this aspect of the invention, the following conditions should be addressed in the design of the device:

1) The RF field should be well separated into two components: the magnetic field generated by RF current in the coils and the electric field generated by the applied RF electromotoric force (voltage) inside the turning and matching capacities.

2) The coils should be well electrically separated to avoid cross-talk among them.

3) The ratio of power $P_L$ when the patient or phantom is loaded in the device to power $P_E$ when the device is empty that is $\Gamma = P_L/P_E$ should be a big number. that means that the Q-value of individual coils should be high.

The distribution of thermal energy across the active volume inside of the device and the corresponding distribution of temperatures should be known for the device empty and the device loaded by a phantom. That could be accomplished by calorimetric methods, preferably by a lattice of liquid alcohol thermometric immersed in small test tubes filled with a conductive electrolyte.

4) Instead of simple rings, more complex rings can be used to increase the field penetration along the coil axis. Namely, let a ring with radius A has n turns and let there be second ring with radius B with m turns, located concentrically in the same plane and connected in series with the first ring and wound in opposite direction with respect to the first ring. let, further, the ratio A:B be equal to n:m where n and m are integers and n>m. Then the field along the x axis is $$H(x) = \frac{\mu_0 I}{4\pi} \left\{ \frac{nA^2}{(A^2+x^2)^{\frac{3}{2}}} - \frac{m\left(\frac{m}{n}\right)^2 A^2}{\left[\left(\frac{m}{n}A\right)^2 + x^2\right]^{\frac{3}{2}}} \right\}$$

that is H(0)=0. The maximum field is then found from $$\frac{dH(x)}{dx} = 0$$

and it is seen to be at $$x = \pm A * \left(\frac{m}{n}\right)^{\frac{3}{5}} * \sqrt{\frac{1 - \left(\frac{m}{n}\right)^{\frac{4}{5}}}{1 - \left(\frac{m}{n}\right)^{\frac{6}{5}}}} \; ; n > m$$

The invention claimed is:

1. An apparatus for treating a subject comprising:
   a stationary array of radio frequency (RF) coils, said array comprising one or more main coils and one or more focusing coils; and
   a signal generator electrically coupled to the stationary array of RF coils through a power amplifier, and configured to sequentially apply a first RF signal to the one or more main coils and a second RF signal to the one or more focusing coils, such that the one or more main coils and the one or more focusing coils are not on simultaneously,
   wherein the main coils generate a peak RF energy at a distance of one inch that is stronger than the peak RF energy generated by the focusing coils, and
   wherein the first and second RF signals produce a strong RF field at a focused location within the body of the subject.

2. The apparatus of claim 1, wherein the signal generator is arranged to actuate the main and focusing coils in alternating sequence.

3. The apparatus of claim 1, wherein the one or more focusing coils comprises two focusing coils, and the one or more central coils comprises two central coils, and wherein each of the central coils is positioned between the focusing coils.

4. The apparatus of claim 3, wherein two of the central coils overlap one another.

5. The apparatus of claim 1, further comprising a cylindrical housing of conductive material, wherein the array comprises one main coil housed in the cylindrical housing, and one focusing coil disposed at the mouth of the cylindrical housing and concentric to the main coil.

6. The apparatus of claim 1, wherein the phase of the first RF signal is offset by 180 degrees from the phase of the second RF signal.

7. A method of heating tissues in the body of a subject comprising the steps of:
   providing an array of RF coils within a distance from the subject such that the array is capable of focusing an RF energy on the tissues of the subject, wherein the array comprises one or more focusing coils and one or more main coils;
   actuating the one or more main coils to produce a first RF signal;
   actuating each of the one or more focusing coils to produce a second RF signal, wherein the main and focusing coils are actuated sequentially such that they are not on simultaneously, and wherein the main and focusing coils are actuated such that the main coils generate a peak RF energy at a distance of one inch that is stronger than the peak RF energy generated by the focusing coils; and
   using the first and second RF signals, producing a strong RF field at a focused location within the body of the subject.

8. The method of claim 7, wherein the focusing coils are actuated to produce a second RF signal that is 180 degrees out of phase from the first RF signal.

9. An apparatus for generating a focused radio frequency signal, comprising:

a plurality of radio frequency coils spaced apart and disposed on an outer surface of a cylindrical housing, wherein each respective one of the plurality of radio frequency coils operates at a different resonant frequency;

a plurality of radio frequency input circuits, each respective radio frequency input circuit connected to a respective one of the plurality of radio frequency coils through a respective hole; and a power switching circuit connected to the plurality of radio frequency input circuits and configured to control the on-and-off powering of the radio frequency coils in a predetermined time sequence such that no two of the plurality of radio frequency coils are on simultaneously.

10. The apparatus of claim 9, wherein each of the plurality of radio frequency coils is configured to produce an RF signal having a frequency between 13.6 MHz and 15 MHz.

11. The apparatus of claim 9, wherein the plurality of radio frequency coils comprises a substantially circular array of coils.

12. The apparatus of claim 11, wherein the power switching circuit is operable to, for each of the radio frequency coils, switch the coil on for a predetermined period of time, and not switch on any coil adjacent to that coil for a period of time at least four times longer than the predetermined period of time.

13. The apparatus of claim 9, wherein the power switching circuit is operable to, for each of the radio frequency coils, switch the coil on for a predetermined period of time to produce an RF pulse, and switch the coil off for a period of time at least seven times longer than the amount of time that the coil was switched on.

* * * * *